United States Patent [19]
Kruse et al.

[11] Patent Number: 4,839,371
[45] Date of Patent: Jun. 13, 1989

[54] 3-ARALKYL-2-MERCAPTOYRIDINES AS DOPAMINE-β-HYDROXYLASE INHIBITORS

[75] Inventors: Lawrence I. Kruse, Hertfordshire, England; Stephen T. Ross, Berwyn, Pa.

[73] Assignee: SmithKline Beckman Corporation, Philadelphia, Pa.

[21] Appl. No.: 97,988

[22] Filed: Sep. 17, 1987

[51] Int. Cl.$^4$ .................... A61K 31/44; C07D 213/70
[52] U.S. Cl. .................... 514/345; 546/290; 546/301; 546/302; 546/303
[58] Field of Search ............... 546/290, 301, 303, 302; 514/345

[56] References Cited

U.S. PATENT DOCUMENTS

| | | | |
|---|---|---|---|
| 3,853,900 | 12/1974 | Shone | 546/290 |
| 4,487,761 | 12/1984 | Cole et al. | 514/345 |
| 4,532,331 | 7/1985 | Frazee et al. | 548/343 |

Primary Examiner—Richard A. Schwartz
Assistant Examiner—Zinna Northington
Attorney, Agent, or Firm—Mary E. McCarthy; Stuart R. Suter; Alan D. Lourie

[57] ABSTRACT

Disclosed are novel substituted 3-aralkyl-2-mercaptopyridines of the structure:

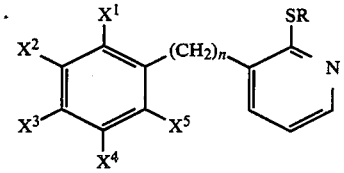

processes for their preparation, intermediates useful in their preparation, pharmaceutical compositions containing them and their use in therapy in particular as dopamine-β-hydroxylase inhibitors.

10 Claims, No Drawings

3-ARALKYL-2-MERCAPTOYRIDINES AS DOPAMINE-β-HYDROXYLASE INHIBITORS

The present invention relates to novel substituted 3-aralkyl-2-mercaptopyridines, processes for their preparation, intermediates useful in their preparation, pharmaceutical compositions containing them and their use in therapy in particular as dopamine-β-hydroxylase (DBH) inhibitors.

Compounds that inhibit DBH activity are known and include:

(a) 5-alkylpicolinic acids [See, Suda et al., *Chem. Pharm. Bull.* 17, 2377 (1969); Umezawa et al., *Biochem. Pharmacol.* 19, 35 (1969); Hidaka et al., *Mol. Pharmacol.* 9, 1972 (1973); Miyano et al., *Chem. Pharm. Bull.* 26, 2328 (1978); Miyano et al., *Heterocycles* 14, 755 (1980); Claxton et al., *Eur. J. Pharmacol.* 37, 179 (1976)];

(b) BRL 8242 [See, Claxton et al., *Eur. J. Pharmacol.* 37, 179 (1976)];

(c) 1-alkylimidazole-2-thiols [See, Hanlon et al., *Life Sci.* 12, 417 (1973); Fuller et al., *Adv. Enzyme Regul.* 15, 267 (1976)];

(d) substituted thioureas [See, Johnson et al., *J. Pharmacol. Exp. Ther.* 168, 229 (1969)]; and (e) benzyloxamine and benzylhydrazine [See, Creveling et al., *Biochim. Biophys. Acta* 64, 125 (1962); Creveling et al., *Biochim. Biophys. Acta* 8, 215 (1962); Van De Schoot et al., *J. Pharmacol. Exp. Ther.* 141, 74 (1963); Bloom, *Ann N.Y. Acad. Sci.* 107, 878 (1963)].

(f) fusaric acid derivatives and analogues [See, Runti et al., *Il Farmaco Ed. Sci.* 36, 260 (1980)] for example phenylpicolinic acid, 5-(4-chlorobutyl) picolinic acid, substituted amides of fusaric acid and acids and amides of 5-butydropicolinic acid, 5-aminopicolinic acid 5-hydrazinopicolinic acid, and derivatives thereof.

(g) Hidaka et al., *Molecular Pharmacology*, 9, 172–177 (1972) 5-(3,4-dibromobutyl)picolinic acid and 5-(dimethyldithiocarbamoyl)methylpicolinic acid.

(h) Bupicomide, 5-(n-butyl)picolinamide, is reported by Ehrreich et al., "New Antihypertensive Drugs", Spectrum Publications, 1976, pg. 409–432.

(i) In U.S. Pat. No. 4,532,331 a series of 1-phenyl and 1-phenylalkylimidazole compounds having a mercapto or alkylthio group in the 2-position are disclosed.

(j) U.S. Pat. No. 4,487,761 describes several methylpyridine derivatives isolated from the fermentation broth of a strain of streptoverticillium.

(k) Friedman et al., *Psychosomatic Med.* 40, 107 (1978), report that patients treated with alpha-methyl-DOPA, guanethidine, and reserpine, but not propranolol and diuretics, have lowered DBH levels, although the significance of the observation is uncertain.

As a result there is a continuing need for novel compounds that possess DBH inhibitory activity.

Accordingly to present invention provides compounds of structure (I):

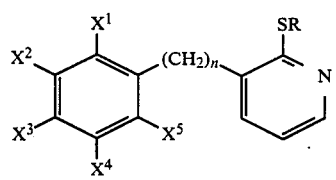

and pharmaceutically acceptable salts thereof, in which, $X^1$ to $X^5$ are each hydrogen, halogen, hydroxy, or $C_{1-4}$alkoxy;

n is 1 to 5; and

R is hydrogen or $C_{1-4}$alkyl.

It will be appreciated that when R is hydrogen, structure (I) covers the tautomeric forms thereof that is compounds of structure (Ia).

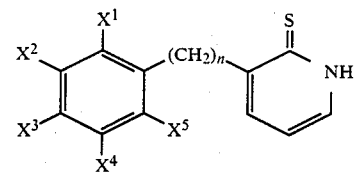

Suitably $X^1$ to $X^5$ are all hydrogen. Preferably, one of $X^1$ to $X^5$ is halogen and the others are hydrogen. More preferably two of $X^1$ to $X^5$ are halogen and the others are hydrogen. Most preferably $X^1$, $X^3$, and $X^5$ are hydrogen and $X^2$ and $X^4$ are both halogen in particular fluorine.

Suitably n is 2, 4, or 5; preferably n is 1 or 3, most preferably n is 1.

Particular compounds of this invention include:
3-(3,5-difluorobenzyl)-2-mercaptopyridine;
3-(3-fluorobenzyl)-2-mercaptopyridine;
3-benzyl-2-mercaptopyridine;
3-(3,5-difluorophenylpropyl)-2-mercaptopyridine;
3-(3-fluorophenylpropyl)-2-mercaptopyridine;
3-(phenylpropyl)-2-mercaptopyridine.

A further aspect of the present invention provides a process for the preparation of compounds of structure (I) and pharmaceutically acceptable salts thereof, which process comprises reacting a compound of the structure (II):

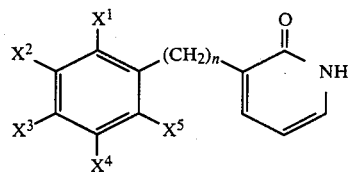

wherein $X^1$ to $X^5$ are each hydrogen, halogen, or $C_{1-4}$alkoxy and n is 1 to 5; with a reagent that converts the keto group to a thione and optionally, converting a $C_{1-4}$alkoxy into a hydroxy group, converting a compound of structure (I) in which R is hydrogen to one in which R is $C_{1-4}$alkyl and optionally forming a pharmaceutically acceptable salt.

Suitable reagents for this conversion will be apparent to those skilled in the art and include phosphorous pentasulphide ($P_2S_5$) in the presence of pyridine as a solvent or Lawesson's reagent in the presence of toluene as a solvent. Compounds of structure (I) in which R is $C_{1-4}$alkyl are prepared by alkylating the corresponding compound of structure (I) where R is hydrogen with an alkyl halide, for example, methyl iodide in methanol, by procedures known to those skilled in the art. Other alkyl halides such as methyl bromide or methyl chloride, in appropriate solvents in the presence of a base such as sodium hydroxide or sodium carbonate, can be substituted for methyl iodide. Further, the compounds of structure (I) in which R is an alkyl group other than methyl are prepared by substituting an alkyl halide such as butyl iodide, for the methyl halide to yield the desired 5-substituted-3-aralkyl-2-mercaptopyridines of the invention.

Pharmaceutically acceptable acid addition salts of compounds of the invention are formed with appropriate strong or moderately strong organic or inorganic acids by methods known in the art. For example, the base is reacted with a suitable inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the salts which are included in this invention are maleate, fumarate, lactate, oxalate, methanesulfonate, ethanesulfonate, benzenesulfonate, tartrate, citrate, hydrochloride, hydrobromide, sulfate, phosphate, quinate, and nitrate salts.

Compounds of the structure (II), which are themselves novel and form a further aspect of the invention, can be prepared from compounds of the structure (III):

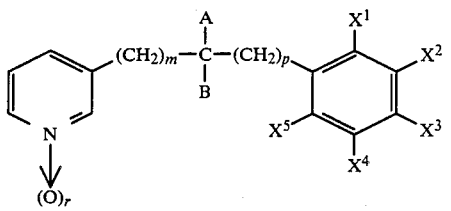

in which:

$X^1$ to $X^5$ are hydrogen, halogen or $C_{1-4}$alkoxy;

r is 0 or 1;

A and B are both hydrogen or can be taken together to form a keto group; and m and p are each 0 to 4 but m+p is not greater than 4.

For example compounds of the formula (II) can be prepared from suitable compounds of the structure (III) in which r is 1 and A and B are both hydrogen that is compounds of the structure (IV):

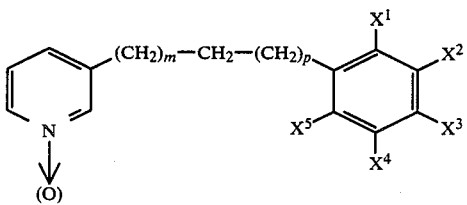

by reaction with a $C_{1-4}$alkanoyl anhydride at elevated temperatures or acetic anhydride in the presence of a base. Suitable bases include, for example, sodium hydroxide, potassium hydroxide, lithium hydroxide, or sodium carbonate.

Following removal of the alkanoyl anhydride at completion of the Polonovski rearrangement reaction, with compound of structure II is isolated by treatment with a base and separation from the unwanted product isomer; that is a compound of the structure (IIa):

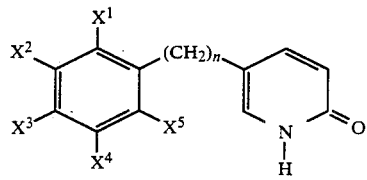

Compounds of structure (II) are less soluble in organic solvents than those of structure (IIa). Identification of compounds of structure II is made by proton-NMR spectroscopy.

Further, compounds of the structure (IV) can be prepared from compounds of the structure (III) in which r is 0, A and B are both hydrogen, and m and p and $X^1$ and $X^5$ are as described for structure (III); that is compounds of the structure (V):

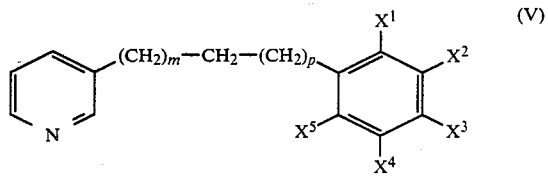

The reaction can be carried out in the presence of a suitable oxidizing agent known to those skilled in the art, for example hydrogen peroxide or hydrogen peroxide/ethanoic acid or $CF_3CO_2H$; most preferably the oxidation is carried out using 3-chloroperbenzoic acid.

Furthermore, compounds of the structure (V) can be prepared from compounds of the structure (III) in which r is 0 and A and B together form a keto group, and m and p and $X^1$ to $X^5$ are as described for structure (III) that is compounds of the structure (VI):

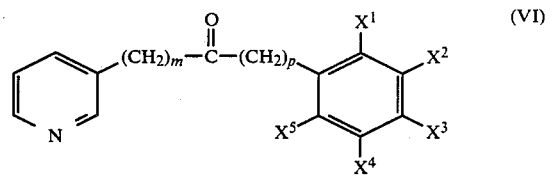

The reaction can be carried out in the presence of a reducing agent. Suitable reagents will be apparent to those skilled in the art, and include for example, zinc amalgam in hydrochloric acid. Preferably the keto group of structure (VI) is protected as a ketal group during the reaction hereinabove described.

In addition, compounds of the structure (VI) can be prepared by reacting an appropriate 3-substituted pyridine (VII) with an appropriate known metal-derivative of structure (VIII):

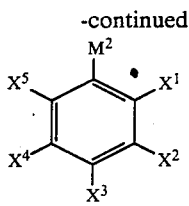

(VIII)

where $X^1$ to $X^5$ are as hereinabove defined and one of $M^1$ and $M^2$ is an alkali metal, preferably lithium, and the other is a cross-lithium reactive group such as cyano or N,N-dialkylcarboxamido.

Preferably, $M^1$ is cyano and $M^2$ is lithium and after the reaction is carried out in the presence of ether, aqueous hydrochloric acid is subsequently added to quench the reaction.

The present invention also provides a method of inhibiting DBH which comprises administering to a mammal in need thereof an effective amount of a compound of structure (I) or a pharmaceutically acceptable salt thereof.

In addition compounds of the structure (I) and pharmaceutically acceptable salts thereof lower blood pressure in vivo and are therefore useful as diuretic, natriuretic, cardiotonic, antihypertensive, antianginal, vasodilatory agents. Further still compounds of the structure (I) and pharmaceutically acceptable salts thereof may be used as antiulcerogenic and antiParkinson agents.

In the methods of the present invention the compounds of structure (I) are usually administered in a standard pharmaceutical composition. The present invention therefore provides in a further aspect pharmaceutical compositions comprising a compound of structure (I) or a pharmaceutically acceptable salt thereof and a pharmaceutically acceptable carrier. Such compositions include those suitable for administration via an appropriate route known to those skilled in the art for example, orally, parenterally, transdermally, rectally, via inhalation or via buccal administration.

The compounds of structure (I) and their pharmaceutically acceptable salts which are active when given orally can be formulated as tablets, capsules, lozenges, and liquids, for example syrups, suspensions, or emulsions.

A liquid formulation will generally consist of a suspension or solution of the compound or pharmaceutically acceptable salt in a suitable liquid carrier(s) for example, ethanol, glycerine, sorbitol, non-aqueous solvent, for example polyethylene glycol, oils, or water with a suspending agent, preservative surfactant, wetting agent, flavoring or coloring agent.

Alternatively, a liquid formulation can be prepared from a reconstitutable powder. For example a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid formulations. Examples of such carriers include magnesium stearate, starch, lactose, sucrose, cellulose and binders, for example, polyvinyl pyrrolidone. The tablet can also be provided with a color film coating, or color included as part of the carrier(s). In addition, acting compound can be formulated in a controlled release dosage form as a table comprising a hydrophilic or hydrophobic matrix.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of structure (I) or a pharmaceutically acceptable salt thereof which is active when administered in this way, with a binding and/or lubricating agent such as polymeric glycols, gelatins or cocoa butter or other low melting vegetable or synthetic waxes or fats.

Compounds of structure (I) and their pharmaceutically acceptable salts which are active on topical administration can be formulated as transdermal compositions. Such compositions include, for example, a backing, active compound reservoir, a control membrane, liner and contact adhesive.

Typical compositions for inhalation are in the form of a solution, suspension, or emulsion that may be administered in the form of an aerosol using a conventional propellant such a dichlorodifluoromethane or trichlorofluoromethane.

Preferably the composition is in an appropriate unit dosage form. Each dosage unit for oral administration contains preferably from 1 to 250 mg (and for parenteral administration contains preferably from 0.1 to 25 mg) of a compound of the structure (I) or a pharmaceutically acceptable salt thereof calculated as the free acid.

The daily dosage regimen for an adult patient may be, for example, an oral dose of between 1 mg and 1000 mg, preferably between 1 mg and 250 mg, or an intravenous, subcutaneous, or intramuscular dose of between 0.1 mg and 100 mg, preferably between 0.1 mg and 25 mg, of the compound of the structure (I) or a pharmaceutically acceptable salt thereof calculated as the free base, the compound being administered 1 to 4 times per day. Suitably the compounds will be administered for a period of continuous therapy, for example for a week or more. In addition, the compounds of this invention may be co-administered with other pharmaceutically active compounds, for example in combination, concurrently or sequentially.

The following examples illustrate the invention. Temperature are recorded in degrees centigrade.

EXAMPLE 1

3-(3-Fluorobenzoyl)pyridine

A solution of 3-bromofluorobenzene (25.0, 0.143 mol) in ether (250 ml) was cooled to $-78°$ C. and stirred during the dropwise addition of a 2.3 M solution of tert-butyllithium in pentane (62 ml, 0.143 mol). After the addition was completed, stirring was continued for 15 minutes and a solution of 3-cyanopyridine (14.9 g, 0.143 mol) in ether (125 ml) was added dropwise. The resulting mixture was allowed to warm to 15° C. and a solution of 12 N HCl (36 ml) in H₂O (90 ml) was added dropwise. After the resulting light yellow solution had stirred for 30 minutes, 10% NaOH was added to give a pH of 10, and the ether layer was separated. The aqueous phase was extracted twice with ether, the combined ether extracts were concentrated and the residue was distilled to yield 21.3 g (74%) of 3-(3-fluorobenzoyl)-pyridine bp: 112°–128° C./59.99 Nm⁻².

EXAMPLE 2

3-(3,5-Difluorobenzoyl)pyridine

Substituting 1-bromo-3,5-difluorobenzene for 3-bromofluorobenzene and using the procedure of Example 1 yielded (42%) of the title ketone: bp 110°–137° C./53.33 Nm⁻².

EXAMPLE 3

3-(3-Fluorobenzyl)pyridine

Zinc amalgam prepared from zinc (41 g) and HgCl₂ (4.1 g) was stirred in a mixture of 3-(3-fluorobenzoyl)-pyridine (19.0 g, 0.095 mol), H₂O (25 ml) and 12 N HCL (60 ml). The resulting mixture was stirred and heated at reflux for 30 hours. Occasionally during the course of the reaction HCl gas was passed through the mixture, and after 20 hours, additional zinc metal (41 g) was added. After 30 hours the reaction mixture was cooled, decanted, made strongly basic with 10% NaOH, and extracted three times with CH₂Cl₂. The extracts were dried (Na₂SO₄) and concentrated, and the residue was distilled to yield 5.2 g (29%) of 3-(3-fluorobenzyl)pyridine: bp 100°–110° C./79.99 Nm⁻².

EXAMPLE 4

3-(3,5-Difluorobenzyl)pyridine

Substituting 3-(3,5-difluorobenzoyl)pyridine for 3-(3-fluorobenzoyl)pyridine and using the procedure of Example 3 yielded (61%) of 3-(3,5-difluorobenzyl)pyridine: bp 90°–110° C./79.99 Nm⁻².

EXAMPLE 5

3-Benzyl-2-pyridone

A solution of 3-benzylpyridine (50 g, 0.3 mol) in CHCl₃ (500 ml) was stirred during the portionwise addition of 3-chloroperbenzoic acid (60 g, 0.325 mol). The reaction mixture was stirred for 2 hours then diluted with H₂O (200 ml) and made basic to pH 8 with 10% NaOH. The CHCl₃ layer was separated, extracted twice with 5% NaHCO₃ and concentrated to give 57.5 g of crude N-oxide which was used without purification. The crude N-oxide (19.5 g, 0.1 mol) was added cautiously to acetic anhydride (200 ml) which had been heated to 85° C. After the addition was completed, the solution was heated at reflux for 45 minutes, then cooled and concentrated. The residual oil was dissolved in ether and the resulting solution was stirred with ethanol and 40% NaOH until the precipitation of solid was completed. The product was filtered to yield 2.26 g of 3-benzyl-2-pyridone as a white solid: m.p. 158.5°–160° C.

EXAMPLE 6

3-(3-Fluorobenzyl)-2-pyridone

Substituting 3-(3-fluorobenzyl)pyridine for 3-benzylpyridine and using the procedure of Example 5 yielded 3-(3-fluorobenzyl)-2-pyridone, m.p. 110° C.

EXAMPLE 7

3-(3,5-Difluorobenzyl)-2-pyridone

Substituting of 3-(3,5-difluorobenzyl)pyridine for 3-benzylpyridine and using the procedure of Example 5 yielded 3-(3,5-difluorobenzyl)-2-pyridone (TLC Rf 0.3 with 10% CH₃OH—CHCl₃).

EXAMPLE 8

3-Benzyl-2-mercaptopyridine

3-Benzyl-2-pyridone (1.65g, 8.9 mmol) and P₂S₅ (1.98 g, 8.9 mmol) were heated at reflux for 22 hours under argon in pyridine (17ml), and then allowed to stand overnight at ambient temperature. The mixture was diluted with brine and extracted with ethyl acetate. The ethyl acetate extracts were dried (MgSO₄) and purified by chromatography using 5% CH₃OH—CH₂Cl₂ as eluant followed by recrystallization from CH₂Cl₂—ether—hexane to yield 300 mg (15%) of 3-benzyl-2-mercaptopyridine: m.p. 129°–130° C. That the 3-benzyl isomer had been isolated was confirmed by use of proton NMR spectroscopy.

EXAMPLE 9

3-(3-Fluorobenzyl)-2-mercaptopyridine

A mixture of 3-(3-fluorobenzyl)-2-pyridone and Lawesson's reagent in toluene was heated at reflux for 1 hours, then cooled and decanted. The residue was washed with CH₂Cl₂ and the combined organic layers were concentrated. The resulting solid was purified by flash chromatography using 5% CH₃OH—CH₂Cl₂ as eluant followed by recrystallization from CH₂Cl₂-ether-hexane to yield 35% of 3-(3-fluorobenzyl)-2-mercaptopyridone: m.p. 159°–160° C. That the 3-(3-fluorobenzyl) isomer had been isolated was confirmed by use of proton NMR spectroscopy.

Lawesson's reagent,

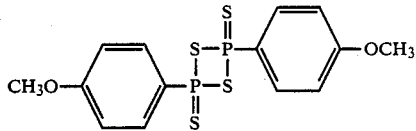

EXAMPLE 10

3-(3,5-Difluorobenzyl)-2-mercaptopyridine

Substituting 3-(3,5-difluorobenzyl)pyridone for 3-benzylpyridone and using the procedure of Example 8 yielded (35%) 3-(3,5-difluorobenzyl)-2-mercaptopyridine: m.p. 195°–197° C. That the 3-(3,5-difluorobenzyl) isomer had been isolated was confirmed by use of proton NMR spectroscopy.

EXAMPLE 11

3-(3,5-Difluorobenzyl)-2-methylmercaptopyridine

The reaction of 3-(3,5-difluorobenzyl)pyridine-2-thione, prepared in Example 10, with methyl iodide in methanol in the presence of base by standard techniques yields 3-(3,5-difluorobenzyl)-2-methylmercaptopyridine.

EXAMPLE 12

An oral dosage form for administering the presently invented compounds is produced by screening, mixing, and filling into hard gelatin capsules the ingredients in the proportions shown in Table I, below.

TABLE I

| Ingredients | Amounts |
| --- | --- |
| 3-(3,5-Difluorobenzyl)-2-mercaptopyridine | 50 mg |
| magnesium stearate | 5 mg |
| lactose | 75 mg |

EXAMPLE 13

The sucrose, calcium sulfate dihydrate, and structure (I) compound shown in Table II below, are mixed and granulated in the proportions shown with a 10% gelatin solution. The wet granules are screened, dried, mixed with the starch, talc, and stearic acid, screened, and compressed into a tablet.

TABLE II

| Ingredients | Amounts |
| --- | --- |
| 3-(3-Fluorobenzyl)-2-mercaptopyridine | 100 mg |
| calcium sulfate dihydrate | 150 mg |
| sucrose | 20 mg |
| starch | 10 mg |
| talc | 5 mg |
| stearic acid | 3 mg |

EXAMPLE 14

3-(3,5-Difluorobenzyl)-2-mercaptopyridine hydrochloride, 75 mg, is dispursed in 25 ml or normal saline to prepare an injectable preparation.

EXAMPLE 15

Because the compounds of structure (I) inhibit DBH activity, they have therapeutic value as diuretic, natriuretic, cardiotonic, antihypertensive, antianginal, and vasodilator agents, as well as antiulcerogenic and anti-Parkinson agents. Listed in Table I are the compounds of the invention that were tested for in vitro DBH inhibition by a standard procedure for assaying conversion of tyramine to octopamine in the presence of DBH. J.J. Pisano, et al., *Biochim. Biophys. Acta,* 43, 566–568 (1960). Octopamine was assayed following sodium periodate oxidation to p-hydroxybenzaldehyde by measuring spectrophotometric absorbance at 330 nm. In Table III, inhibition is given in micromolar concentration of compound at which DBH activity was halved ($IC_{50}$). By this test, fusaric acid had an $IC_{50}$ of 0.8 micromolar.

TABLE III

| Compound | DBH $IC_{50}$ ($\mu M$) |
| --- | --- |
| 3-(3-Fluorobenzyl)-2-mercaptopyridine | 500 |
| 3-(3,5-Difluorobenzyl)-2-mercaptopyridine | 134 |

Further, spontaneously hypertensive rats were treated with a suspension or solution of 3-(3,5-difluorobenzyl)-2-mercaptopyridine at a dose of 50 mg/kg intraperitoneally, and mean arterial blood pressure was monitored for 260 minutes using indwelling cannulae in the tail arteries. When compared to vehicle-treated controls, animals treated with the compounds of the invention exhibited significant blood pressure reductions within approximately 30 minutes after treatment. Maximal blood pressure reduction was approximately 50 to 55 mm Hg.

Contemplated equivalents of structure (I) compounds are compounds that upon administration to mammals, including humans, are metabolized to structure (I) compounds or metabolized to any structure (I) compound active metabolites in sufficient amounts of produce the physiologic activity of structure (I) compounds. Such compounds also would be included in the invented pharmaceutical compositions and used in the invented methods.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound of structure (I):

$$\begin{array}{c} X^1 \quad SR \\ X^2 \underset{X^3}{\underset{X^4}{\bigcirc}} (CH_2)_n \underset{X^5}{\bigcirc}_N \end{array} \quad (I)$$

in which:
$X^1$ to $X^5$ are hydrogen, halogen, hydroxy, or $C_{1-4}$alkoxy;
n is 1 to 5; and
R is hydrogen or $C_{1-4}$alkyl; or a pharmaceutically acceptable salt thereof.

2. A compound as claimed in claim 1 in which n is 1 or 3, $X^1$, $X^3$, and $X^5$ are hydrogen and $X^2$ and $X^4$ are both halogen.

3. A compound as claimed in claim 1 which is 3-(3,5-difluorobenzyl)-2-mercaptopyridine.

4. A compound as claimed in claim 1 which is:
3-(3-fluorobenzyl)-2-mercaptopyridine;
3-benzyl-2-mercaptopyridine;
3(3,5-difluorophenylpropyl)-2-mercaptopyridine;
3-(3-fluorophenylpropyl)-2-mercaptopyridine; or
3-(phenylpropyl)-2-mercaptopyridine.

5. A pharmaceutical composition for inhibiting dopamine-$\beta$-hyroxylase activity comprising an effective amount of a compound of claim 1 and a pharmaceutically acceptable carrier.

6. A pharmaceutical composition of claim 5 wherein the compound is 3-(3,5-difluorobenzyl)-2-mercaptopyridine.

7. A pharmaceutical composition of claim 5 wherein the compound is:
3-(3-fluorobenzyl)-2-mercaptopyridine;
3-benzyl-2-mercaptopyridine;
3-(3,5-difluorophenylpropyl)-2-mercaptopyridine;
3-(3-fluorophenylpropyl)-2-mercaptopyridine; or
3-(phenylpropyl)-2-mercaptopyridine.

8. A method of inhibiting DBH activity which comprises administering to a mammal in need thereof an effective amount of a compound as claimed in claim 1.

9. A method of claim 8 wherein the compound is 3-(3,5-difluorobenzyl)-2-mercaptopyridine.

10. A method of claim 8 wherein the compound is:
3-(3-fluorobenzyl)-2-mercaptopyridine;
3-benzyl-2-mercaptopyridine;
3-(3,5-difluorophenylpropyl)-2-mercaptopyridine;
3-(3-fluorophenylpropyl)-2-mercaptopyridine; or
3-(phenylpropyl)-2-mercaptopyridine.

* * * * *